United States Patent [19]

Berg

[11] Patent Number: 5,439,561

[45] Date of Patent: * Aug. 8, 1995

[54] SEPARATION OF 3-METHYL-2-BUTANOL FROM 2-PENTANOL BY AZEOTROPIC

[75] Inventor: Lloyd Berg, 1314 S. Third Ave., Bozeman, Mont. 59715

[73] Assignee: Lloyd Berg, Bozeman, Mont.

[ * ] Notice: The portion of the term of this patent subsequent to Apr. 18, 2012 has been disclaimed.

[21] Appl. No.: 345,906

[22] Filed: Nov. 28, 1994

[51] Int. Cl.$^6$ .......... B01D 3/36; C07C 29/82; C07C 31/125
[52] U.S. Cl. .......... 203/58; 203/60; 203/63; 203/67; 203/70; 568/913
[58] Field of Search .......... 203/58, 63, 70, 60, 203/67; 568/913

[56] References Cited

U.S. PATENT DOCUMENTS

| | | | |
|---|---|---|---|
| 2,483,246 | 9/1949 | Stribley | 203/60 |
| 2,551,584 | 5/1951 | Carlson et al. | 203/63 |
| 2,552,911 | 5/1951 | Steitz | 203/69 |
| 2,575,243 | 11/1951 | Carlson et al. | 203/60 |
| 4,969,977 | 11/1990 | Berg | 203/65 |

Primary Examiner—Wilbur Bascomb, Jr.

[57] ABSTRACT

3-Methyl-2-butanol is difficult to separate from 2-pentanol by conventional distillation or rectification because of the proximity of their boiling points. 3-Methyl-2-butanol can be readily separated from 2-pentanol by azeotropic distillation. Effective agents are 2,2-dimethyl butane, ethyl acetate and dioxane.

1 Claim, No Drawings

SEPARATION OF 3-METHYL-2-BUTANOL FROM 2-PENTANOL BY AZEOTROPIC

FIELD OF THE INVENTION

This invention relates to a method for separating 3-methyl-2-butanol from 2-pentanol using certain organic liquids as the agent in azeotropic distillation.

DESCRIPTION OF PRIOR ART

Azeotropic distillation is the method of separating close boiling compounds or azeotropes from each other by carrying out the distillation in a multiplate rectification column in the presence of an added liquid, said liquid forming an azeotrope with one or both of the compounds to be separated. Its presence on each plate of the rectification column alters the relative volatility in a direction to make the separation on each plate greater and thus require either fewer plates to effect the same separation or make possible a greater degree of separation with the same number of plates. The azeotrope forming agent is introduced with the feed to a continuous column. The azeotrope forming agent and the more volatile component are taken off as overhead product and the less volatile component comes off as bottoms product. The usual methods of separating the azeotrope former from the more volatile component are cooling and phase separation or solvent extraction.

The usual method of evaluating the effectiveness of azeotropic distillation agents is the change in relative volatility of the compounds to be separated, Table 1 shows the degree of separation or purity obtainable by theoretical plates at several relative volatilities, Table 1 shows that a relative volatility of at least 1.2 is required to get an effective separation by rectification.

TABLE 1

Effect of Relative Volatility on Theoretical Stage Requirements.

| Separation Purity, Both Products (Mole Fraction) | Relative Volatility | | | | | | | |
|---|---|---|---|---|---|---|---|---|
| | 1.02 | 1.1 | 1.2 | 1.3 | 1.4 | 1.5 | 2.0 | 3.0 |
| | Theoretical Stages at Total Reflux | | | | | | | |
| 0.999 | 697 | 144 | 75 | 52 | 40 | 33 | 19 | 12 |
| 0.995 | 534 | 110 | 57 | 39 | 30 | 25 | 14 | 9 |
| 0.990 | 463 | 95 | 49 | 34 | 26 | 22 | 12 | 7 |
| 0.98 | 392 | 81 | 42 | 29 | 22 | 18 | 10 | 6 |
| 0.95 | 296 | 61 | 31 | 21 | 16 | 14 | 8 | 4 |
| 0.90 | 221 | 45 | 23 | 16 | 12 | 10 | 5 | 3 |

There are a number of commercial processes which produce complex mixtures of oxygenated organic compounds, e.g. the Fischer-Tropsch process. In this mixture, a series of homologous alcohols are often produced. Two of the commonest alcohols in this mixture are -methyl-2-butanol and 2-pentanol. 3-Methyl-2-butanol boils at 112° C. and 2-pentanol at 118° C. The relative volatility between these two is 1.35 which makes it difficult to separate them by conventional rectification. Azeotropic distillation would be an attractive method of effecting the separation of 3-methyl-2-butanol from 2-pentanol if agents can be found that (1) will create a large apparent relative volatility between 3-methyl-2-butanol and 2-pentanol and (2) are easy to recover from 3-methyl-2-butanol. Table 2 shows the relative volatlity required to obtain 99% purity. With no agent, the relative volatility is 1.35 and 42 actual plates are required. With an agent giving a relative volatility of 2.4, only 15 plates are required.

TABLE 2

Theoretical and Actual Plates Required vs. Relative Volatility for 3-Methyl-2-butanol-2-Pentanol Separation

| Relative Volatility | Theoretical Plates Required At Total Reflux, 99% Purity | Actual pLtes Required 75% Efficiency |
|---|---|---|
| 1.35 | 31 | 42 |
| 1.5 | 23 | 31 |
| 2.4 | 11 | 15 |

OBJECTIVE OF THE INVENTION

The object of this invention is to provide a process or method of azeotropic distillation that will enhance the relative volatility of 3-methyl-2-butanol from 2-pentanol in their separation in a rectification column. It is a further object of this invention to identify organic compounds which in addition to the above constraints, are stable, can be separated from 3-methyl-2-butanol and recycled to the azeotrope column with little decomposition.

SUMMARY OF THE INVENTION

The objects of this invention are provided by a process for separating 3-methyl-2-butanol from 2-pentanol which entails the use of certain organic compounds as the agent in azeotropic distillation.

DETAILED DESCRIPTION OF THE INVENTION

I have discovered that certain organic compounds will greatly improve the relative volatility of 3-methyl-2-butanol to 2-pentanol and permit the separation of 3-methyl-2-butanol from 2-pentanol by rectification when employed as the agent in azeotropic distillation. Table 3 lists the compounds that I have found to be effective. They are ethyl ether, 3-methyl pentane, dimethoxymethane, t-butyl methyl ether, t-amyl methyl ether, 2,2-dimethyl butane, pentane, dioxane, methylene chloride carbon tetrachloride, n-butyronitrile and ethyl acetate.

TABLE 3

Effective Azeotropic Distillation Agents For Separating 3-Methyl-2-butanol From 2-Pentanol

| Compounds | Relative Volatility |
|---|---|
| None | 1.35 |
| 3-Methyl pentane | 1.5 |
| Dimethoxymethane | 1.45 |
| t-Butyl methyl ether | 1.45 |
| 2,2-Dimethyl butane | 1.55 |
| Pentane | 1.5 |
| Dioxane | 2.4* |
| Methylene chloride | 1.5 |
| Carbon tetrachloride | 1.45 |
| n-Butyronitrile | 1.45 |
| t-Amyl methyl ether | 1.5 |
| Ethyl acetate | 1.6 |
| Ethyl ether | 1.5 |

*Data Obtained In A Multiplate Column

THE USEFULNESS OF THE INVENTION

The usefulness or utility of this invention can be demonstrated by referring to the data presented in Tables 2 and 3. All of the successful agents show that 3-methyl-2-butanol can be separated from 2-pentanol by means of azeotropic distillation in a rectification column and that the ease of separation as measured by relative volatility is considerable.

WORKING EXAMPLES

Example 1

Five grams of 3-methyl-2-butanol, fifteen grams of 2-pentanol and twenty grams of ethyl acetate were charged to a vapor-liquid equilibrium still and refluxed for twelve hours. Analysis indicated a vapor composition of 16.2% 3-methyl-2-butanol, 83.8% 2-pentanol; a liquid composition of 10.9% 3-methyl-2-butanol, 89.1% 2-pentanol. This is a relative volatility of 1.6.

Example 2

Fifty grams of 3-methyl-2-butanol, fifty grams of 2-pentanol 150 grams of dioxane were placed in the stillpot of a 5.6 theoretical plate glass perforated plate rectification column and refluxed for four hours. The overhead composition was 99.2% 3-methyl-2-butanol, 0.8% 2-pentanol; the bottoms composition was 48.1% 3-methyl-2-butanol, 51.9% 2-pentanol. This is a relative volatility of 2.4.

I claim:

1. A method for recovering 3-methyl-2-butanol from a mixture of 3-methyl-2-butanol and 2-pentanol which comprises distilling a mixture of 3-methyl-2-butanol and 2-pentanol in the presence of an azeotrope forming agent, recovering the 3-methyl-2-butanol and the azeotrope forming agent as overhead product and obtaining the 2-pentanol as bottoms product, wherein said azeotrope forming agent consists of one material selected from the group consisting of ethyl ether, t-butyl methyl ether, t-amyl methyl ether, 3-methyl pentane, pentane, 2,2-dimethyl butane, dimethoxymethane, dioxane, ethyl acetate, n-butyronitrile, methylene chloride and carbon tetrachloride.

* * * * *